US009752107B2

(12) United States Patent
Bock et al.

(10) Patent No.: US 9,752,107 B2
(45) Date of Patent: Sep. 5, 2017

(54) COMPOSITIONS CONTAINING CLEANING PARTICLES

(75) Inventors: Thorsten Bock, Feldkirch (AT); Ulrich Salz, Lindau (DE); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/008,674

(22) Filed: Jan. 18, 2011

(65) Prior Publication Data
US 2011/0217676 A1    Sep. 8, 2011

(30) Foreign Application Priority Data

Mar. 5, 2010    (EP) ..................................... 10155660

(51) Int. Cl.
| | | |
|---|---|---|
| A61C 5/04 | (2006.01) | |
| C11D 7/20 | (2006.01) | |
| C11D 3/12 | (2006.01) | |
| C11D 7/02 | (2006.01) | |
| C11D 11/00 | (2006.01) | |
| C11D 17/00 | (2006.01) | |
| A61C 8/00 | (2006.01) | |
| A61C 13/00 | (2006.01) | |

(52) U.S. Cl.
CPC .............. *C11D 7/20* (2013.01); *C11D 3/1213* (2013.01); *C11D 7/02* (2013.01); *C11D 11/0023* (2013.01); *C11D 17/0013* (2013.01); *A61C 8/00* (2013.01); *A61C 13/0003* (2013.01)

(58) Field of Classification Search
CPC ......... C11D 3/042; C11D 3/044; C11D 3/046; C11D 3/048; C11D 3/06; C11D 7/02; C11D 11/0023; A61C 8/00
USPC ..... 433/216, 226; 134/2; 510/161, 396, 397, 510/508; 424/49
See application file for complete search history.

(56) References Cited

U.S. PATENT DOCUMENTS

| | | | |
|---|---|---|---|
| 3,954,961 A | | 5/1976 | Colodney et al. |
| 3,957,964 A | * | 5/1976 | Grimm, III ............... A61K 8/11 424/10.4 |
| 4,321,042 A | * | 3/1982 | Scheicher ................... 433/201.1 |
| 4,986,981 A | * | 1/1991 | Glace ....................... A61K 8/26 424/49 |
| 5,203,698 A | * | 4/1993 | Blake et al. ..................... 433/88 |
| 6,231,343 B1 | | 5/2001 | Ishibashi et al. |
| 7,741,262 B2 | * | 6/2010 | Smith et al. .................. 510/227 |
| 2002/0028288 A1 | | 3/2002 | Rohrhaugh et al. |
| 2005/0069501 A1 | * | 3/2005 | Ibrahim et al. ................. 424/53 |
| 2008/0262109 A1 | * | 10/2008 | Orlich et al. ................. 514/789 |
| 2008/0280806 A1 | * | 11/2008 | Barteleme et al. ............. 510/446 |
| 2008/0300160 A1 | * | 12/2008 | Smith et al. .................. 510/220 |
| 2009/0042756 A1 | * | 2/2009 | Muzik et al. ................. 510/100 |
| 2009/0090387 A1 | | 4/2009 | Massey Brooker et al. |
| 2009/0130150 A1 | * | 5/2009 | Gazzaniga ............... A61K 8/24 424/401 |
| 2010/0203092 A1 | * | 8/2010 | Ley .......................... A61K 8/24 424/401 |
| 2010/0234262 A1 | * | 9/2010 | Smith et al. ................... 510/161 |

FOREIGN PATENT DOCUMENTS

| | | |
|---|---|---|
| DE | 10026868 | 12/2001 |
| GB | 1414678 | 11/1975 |
| JP | S49075742 | 7/1974 |
| JP | 58083609 | 5/1983 |
| JP | 60224612 | 11/1985 |
| JP | 2003514837 | 4/2003 |
| JP | 2009534475 | 9/2009 |
| WO | 0137796 | 5/2001 |
| WO | 2007109327 | 9/2007 |

OTHER PUBLICATIONS

B. Yang, et al., Influence of Saliva Contamination on Zirconia Ceramic Bonding, Dental Materials, 2008, 24, pp. 508-513.
Y. Aboush, Removing Saliva Contamination from Porcelain Veneers before Bonding, The Journal of Prosthetic Dentistry, 1998, 80 (6), p. 649.
A. Quaas, M. Kern, Panavia F 2.0 Bonding to Contaminated Zirconia Ceramic after Different Cleaning Procedures, Dental Materials, 2007, 23, pp. 506-512.
T. Bock, C. Arnhold, F. Meier, U. Salz, Cleaning of Zirconium Oxide Ceramic after Try-In: Effects on Tensile Bond Strength, IAD Conference, 2008.
M. Blatz, A. Sadan, M. Kern, Resin-Ceramic Bonding: A Review of the Literature, The Journal of Prosthetic Dentistry, 2003, 89, pp. 268-274.
S. Kitayama, et al., Effect of Primer Treatment on Bonding of Resin Cements to Zirconia Ceramic, Dental Materials, 2009, pp. 426-432.
M. Kern, VP Thompson, A Simple Method for Universal Testing of Tensile Bond Strength, Dtsch Zahnarztl, 48, 1993, pp. 769-772.
M. Kern, VP Thompson, Bonding to Glass Infiltrated Alumina Ceramic: Adhesive Methods and their Durability, The Journal of Prosthetic Dentistry, 1995, pp. 240-249, 73 (3).
B. Yang, et al., Influence of Contamination on Zirconia Ceramic Bonding, Journal of Dental Research, 2007, 86 (8), pp. 749-753.
http://en.wikipedia.org/wiki/Particle_size, pp. 1-2; Aug. 15, 2012.
Wikipedia, Group(periodic table), http://en.wikipedia.org/wiki/Group_(periodic_table), Mar. 9, 2016, pp. 1-4.
Hillen, Dr. Elisabeth, Periodic Table, Römpp Chemistry Dictionary, 1989-1992, pp. 3283-3285 (specifically, p. 3285), Thieme Medical Publishers.

* cited by examiner

*Primary Examiner* — Cris L Rodriguez
*Assistant Examiner* — Mirayda A Aponte
(74) *Attorney, Agent, or Firm* — Ann M. Knab; Thad McMurray

(57) ABSTRACT

A composition, containing a carrier medium and particles based on a metal compound with a weight-average particle diameter of 1 nm to 10 μm is useful to clean metal or ceramic surfaces which are part of a dental restoration or of an implant abutment.

20 Claims, No Drawings

COMPOSITIONS CONTAINING CLEANING PARTICLES

This application claims the benefit of European Patent Application Serial No. 10155660.3, filed Mar. 5, 2010, which is hereby incorporated by reference in its entirety.

FIELD

The present invention relates to a composition for cleaning metal or ceramic surfaces, in particular surfaces of dental restorations or implant abutments.

BACKGROUND

Dental restorations or implant abutments often consist of ceramic materials or of metals which can be adapted to tooth defects in different ways. The restoration is generally inserted into the cavity before securing it in order to check the fit ("try-in"). Even when a rubber dam is used, contamination by protein-containing bodily fluids, such as for instance saliva, dentinal fluid, sulcus fluid, blood, is virtually unavoidable here. The proteins are adsorbed on all clinically common ceramics and metals by strongly ionic to partially covalent interactions. If this is followed by adhesive securing by means of customary adhesion promoters ("primers") and radically curing fixing cements and composites, such protein contaminations lead to a clear weakening of the bonding effect between restoration material and cement or composite.

The problem of protein pollution is the subject of some scientific publications which also discuss different possible solutions. Yang et al., *Dental Materials*, 24:508-513 (2008) describe sandblasting with $Al_2O_3$ particles in order to remove saliva contaminations.

Y. Aboush, *J. Prosth. Dent.*, 80(6):649 (1998), recommends cleaning porcelain surfaces with phosphoric acid.

Quaas et al., *Dental Materials*, 23:506-512 (2007), compare air abrasion with $Al_2O_3$ particles and treatment with 37% phosphoric acid or with isopropanol in order to remove saliva contaminations. Air abrasion proved to be the most effective for cleaning zirconia ceramic. Yang et al., *J. Dent. Res.*, 86(8):749-753 (2007) come to comparable results.

T. Bock, U. Salz, *IAD Conference* (2008), Xi'An (CN)) achieved a maximum bonding strength to $ZrO_2$ after cleaning with 2% NaOCl.

However, it was shown that on metal oxides and base metals the phosphoric acid cleaning brings with it a decrease in the bond strength compared with uncontaminated, uncleaned reference samples. Nor can protein adsorbates be completely removed by the hitherto available non-abrasive mechanical methods (e.g. water jet, polishing brushes, ultrasonic bath) before the adhesive securing of restoration materials. Even the combined use of mechanical cleaning methods with the available cleaning agents, such as e.g. detergent solutions and dental polishing pastes, solvents, such as petrol, ethanol or acetone, acids, lyes, oxidizing agents, such as carbamide peroxide, hypochlorite or hydrogen peroxide, or solubilization aids, such as urea, does not lead to an appreciable improvement in the bonding values.

The only method known in the literature for effectively cleaning protein-contaminated dental ceramic and metal surfaces is blasting with abrasive blasting agents (such as e.g. corundum). The surface abrasion occurring with this method removes all of the adsorbed contaminants and thus makes possible a bond comparable to uncontaminated surfaces. However, the disadvantages are the negative influencing of the fit of the restoration by the abrasion, the incompatibility with abrasion-sensitive veneering materials, the unavoidable damage to delicate intersections, the lack of availability of suitable equipment in dental practices and the barely possible intra-oral applicability. Sandblasting is therefore suitable for clinical situations only under certain conditions.

SUMMARY

An object of the present invention is to provide, within the framework of an adhesive securing of dental restoration materials, a composition for the non-abrasive cleaning of the surfaces of restoration materials, in particular for removing protein contaminations, which does not have the disadvantages of the state of the art. The cleaning composition should be able to be applied simply and with the customary technical equipment of dentists or dental technicians, not require toxic chemicals and have no negative effects on the fit of different restoration materials. Applicability of one and the same cleaning composition to different restoration materials would also be advantageous.

The object is achieved by the use of a composition containing a carrier medium and particles based on a metal compound with a weight-average particle diameter of 1 nm to 10 μm to clean metal or ceramic surfaces, wherein the shape of the particles can be spherical, fibroid or nanofibrillar, typically with an aspect ratio of 10-10,000. Spherical particles are preferred.

The invention is also directed towards a method of cleaning a metal or ceramic surface, including bringing the surface into contact with the above cleaning composition and moving the cleaning composition on the surface.

The present invention furthermore relates to a method of inserting a dental restoration including a cleaning step using the above composition.

DETAILED DESCRIPTION

The cleaning composition used according to the invention contains a carrier medium and particles based on a metal compound with a weight-average particle diameter of 1 nm to 10 μm, also called "cleaning particles" in the following.

The individual particles preferably have particle diameters of 1 nm to 500 nm, preferably 1 to 300 nm and particularly preferably 1 to 200 nm Nanoparticles with particle sizes of 1 to 100 nm and most preferably 1 to 50 nm are quite particularly preferred.

Spherical particles are preferably used according to the invention. "Spherical" here means that in any direction the particles have a diameter which differs by at most 10% from the diameter in another direction. In the case of non-spherical particles, by particle diameter is meant the equivalent diameter (surface-equivalent ball diameter). The surface-equivalent ball diameter is the diameter of a ball which has the same surface area as the particle investigated. The terms particle diameter and particle size are here used synonymously. The cleaning particles can be porous or preferably non-porous.

In the case of agglomerated or aggregated particles, the above statements apply to the agglomerates or aggregates.

In preferred embodiments, the cleaning particles have a weight-average diameter in the range from 1 nm to 500 nm, preferably from 1 nm to 100 nm, quite particularly preferably from 1 to 50 nm and most preferably from 2 to 25 nm. The particle size is determined, unless otherwise indicated, by dynamic light scattering.

The cleaning particles of the present invention are composed of a metal compound in which the metal is preferably selected from metals of the 3rd main group of the CAS and IUPAC-old numbering systems, such as for instance aluminium; subgroup metals, such as for instance scandium, yttrium, titanium, zinc and zirconium, and lanthanoids, such as for instance ytterbium and cerium of the Periodic Table of the Elements. Mixtures of metal compounds can also be used. The preferred metal compounds are compounds of aluminium, titanium, zirconium and mixtures thereof, wherein zirconium compounds are particularly preferred.

By metal compounds are meant in particular metal oxides, inorganic and organic metal salts. The metal compounds are preferably selected from metal chalcogenides, in particular metal oxides; metal halides, such as for instance fluorides, chlorides, bromides and iodides; metal chalcogen halides, in particular metal oxyhalides, e.g. oxychlorides; metal pseudohalides, in particular metal isocyanogens; metal-silicon chalcogenides; metal hydroxides; metal oxide hydroxides, metal nitrates, metal oxynitrates and mixtures thereof. Typical organic metal salts are monocarboxylic acid salts, e.g. acetates, formates, nitrilotriacetates, ethylenediaminetetraacetates; chelate complexes, e.g. acetylacetonate, gluconate, fumarate, tartrate, citrate and iminodisuccinate complexes.

Examples of metal compounds of the particles include aluminium oxide, aluminium oxide hydroxide (e.g. γ-AlO(OH) (boehmite)), zirconium dioxide, titanium dioxide (e.g. rutile), zirconyl chloride, titanium nitrate and zirconyl nitrate, wherein aluminium oxide, aluminium oxide hydroxide, zirconium dioxide, titanium dioxide and mixtures thereof are preferred.

The material and the morphology of the cleaning particles are preferably selected such that they show no or only a small abrasive effect in respect of the surface to be cleaned.

The carrier medium of the cleaning composition according to the invention can be a liquid or a solid medium.

The medium is preferably a liquid, particularly preferably water, including aqueous solutions; an organic solvent, including mixtures of organic solvents, or a mixture of water and organic solvent(s). Aqueous solutions also include solutions of acids, lyes and buffers with a pH of 0 to 14, preferably 7 to 14. Examples of suitable organic solvents include aliphatic and cycloaliphatic $C_2$ to $C_8$ alcohols, aliphatic and cycloaliphatic ketones, e.g. acetone and methyl ethyl ketone; aliphatic and cycloaliphatic ethers, e.g. di-t-butyl ether, methyl t-butyl ether, dioxane, dioxolane and dioxol; sulphoxides, e.g. dimethyl sulphoxide; amides and lactams, e.g. N-methylpyrrolidone; esters, e.g. i-amyl propionate, ethyl acetate and butyl acetate. The cleaning particles are dispersed in the liquid medium.

Solid carrier media can for example be used in fibrillar form (such as e.g. fabrics, bristles, brushes, fleeces, felts, strips, fibres or microfibres), in monolithic and non-monolithic form (such as e.g. blocks, disks, sponges (foams) and spherical bodies). Particle-containing heterogeneous phases or coated solids, such as for instance the bicarbonate powder customary for dental treatments, e.g. Clean Jet from Hager Werke can also be used. By particle-containing heterogeneous phases are meant for example dispersions of the cleaning particles used according to the invention in a polymer matrix.

Polymeric compounds can be used as solid media (such as e.g. polyolefins, polyvinyl compounds, polymethacrylates, polyacrylates, polyesters, polyamides, polyimides, polyetherimides, polyaramides, polyurethanes, polyethers, polyamines, polyureas, polysaccharides, polysiloxanes and high-molecular proteins such as collagen), as well as blends thereof. Polyolefins, polyamides, polyesters, polysiloxanes and polyurethanes are preferred. The solid media for their part can be present in particulate form.

The cleaning particles can be applied to the solid medium for example as a coating, typically with a layer thickness of 0.1 to 50 μm, or dispersed therein.

Examples of solid cleaning compositions include extruded brush fibres e.g. made of melt-compounded thermoplastics with cleaning particles or particle-releasing sponges dispersed therein or preferably adsorbed thereon which are obtained by dispersing cleaning particles in suitable monomers and subsequently producing foam (e.g. polyurethane foams).

The cleaning composition according to the invention can optionally contain further constituents, such as abrasion agents customary in dental prophylaxis and medicine, such as e.g. silica, bicarbonate and polymer particles, wetting agents, flotation aids, detergents, such as e.g. non-ionic, anionic and cationic compounds, preferably non-ionic and cationic compounds, defoamers, stabilizers and further auxiliaries, such as for instance antimicrobial additions, scents, flavour additives, colourants, bleaching agents and preservatives. If liquid carrier media are used, the cleaning composition according to the invention can further optionally contain polymeric thickeners, such as e.g. suitably soluble polyvinyl compounds, polymethacrylates, polyacrylates, polyethers, polyamines, polysilicates, and polysaccharides, as well as thixotropic agents and rheology modifiers such as silicate particles, sheet silicates, aluminates and hydrotalcites. Preferred auxiliary materials are non-ionic or cationic detergents, wetting agents, scents, colourants and preservatives.

The cleaning composition according to the invention with liquid or solid carrier medium preferably contains the cleaning particles in a quantity of 1 to 75 wt.-%, preferably 1 to 50 wt.-%, particularly preferably 5 to 35 wt.-%, in the case of a liquid carrier medium and most preferably 10 to 30 wt.-% in the case of a liquid carrier medium, or particularly preferably 1 to 25 wt.-% in the case of a solid carrier medium, in each case relative to the total weight of the composition.

Compositions which do not contain particles measuring more than 500 nm, particularly preferably more than 250 nm, are particularly preferred.

The liquid carrier medium is preferably contained in the cleaning composition in a quantity of 25 to 99 wt.-%, preferably 50 to 99 wt.-%, particularly preferably 65 to 95 wt.-%, and most preferably 70 to 90 wt.-%, in each case relative to the total weight of the composition. The solid carrier medium is preferably contained in the cleaning composition in a quantity of 25 to 99 wt.-%, preferably 50 to 99 wt.-% and particularly preferably 75 to 99 wt.-%, in each case relative to the total weight of the composition. The optional constituents are preferably contained in a quantity of 0 to 5 wt.-% or 0.001 to 5 wt.-%, particularly preferably 0 to 2.5 wt.-% or 0.001 to 2.5 wt.-%, and most preferably of 0 to 1 wt.-% or 0.001 to 1 wt.-%.

An exemplary cleaning composition with liquid carrier material contains:
(i) 5 to 35 wt.-%, preferably 10 to 30 wt.-%, particles with a weight-average particle diameter of 1 to 100 nm based on a metal compound which is selected from aluminium oxide, aluminium oxide hydroxide, zirconium dioxide, titanium dioxide and mixtures thereof, (ii) 65 to 95 wt.-%, preferably 70 to 90 wt.-%, water or aqueous solution with a pH in the range from 7 to 14, and (iii) 0 to 5 wt.-%, preferably 0 to 2.5 wt.-%, optional constituents, preferably selected from detergents, wetting agents, scents, colourants and preservatives.

In some embodiments, the cleaning composition according to the invention is free of detergents and/or free of scents, colourants, wetting agents and/or bleaching agents.

For reasons of ease of application, it is advantageous if the cleaning composition according to the invention is in gel form, as either is already the case due to the interaction of the individual components or can optionally be accomplished by adding suitable thickeners.

In principle, the cleaning composition according to the invention is suitable for cleaning all metal or ceramic surfaces, such as for instance oxide and silicate ceramic; however, it is preferably used to clean surfaces made of materials used in dental medicine, i.e. materials which are clinically common as dental restoration materials, e.g. dental metals such as titanium, gold, platinum group metals as well as their alloys and chromium-cobalt alloys; dental ceramics such as zirconium dioxide ceramic, aluminium oxide ceramic and silicate ceramics, e.g. lithium disilicate glass ceramic, leucite glass ceramic, leucite apatite glass ceramic and feldspar ceramic.

It has been shown that the cleaning composition according to the invention is particularly suitable for cleaning surfaces which are contaminated by proteins. The proteins can for example originate in bodily fluids, such as for instance saliva, dentinal fluid, sulcus fluid and blood. The cleaning composition is used in particular to remove saliva contaminations, in particular to remove saliva proteins such as for instance phosphorus-containing saliva proteins. As the cleaning composition according to the invention removes even strongly adhering protein layers ("protein adsorbates"), it is particularly suitable for cleaning dental restorations and implant abutments, such as for instance for cleaning inlays, onlays, crowns, bridges, suprastructures and abutments, but also for cleaning tooth structure. Even after only a brief introduction into the oral cavity to check the fit, the dental restorations or implant abutments already have protein contaminations which, if not removed, would have a substantial adverse effect on the subsequently produced bond. Preferably, the cleaning composition according to the invention is used immediately after the try-in. The compositions are also suitable for cleaning the prepared tooth and implants which serve as supports for dental restorations, in particular here exposed parts of implants.

It is supposed that, because of their phosphate groups, proteins from bodily fluids, in particular from saliva, which display a relatively high degree of phosphorylation adhere well to the surfaces of the common restoration materials and that, because of their large surface area, the particles of the cleaning compositions according to the invention can interact strongly with precisely these phosphate groups with the result that the proteins are finally "bonded" to the particles and removed from the surface to be cleaned. The term "bonding" to the particles covers purely physical adsorption, ionic bonding and at least partially covalent bonding. The cleaning action is therefore not based on an abrasive effect of the particles, which was able to be confirmed in experiments.

The method of cleaning the metal or ceramic surface, including the above-described preferred surfaces, typically involves bringing the surface into contact with the above-described cleaning composition, including preferred embodiments, and moving the cleaning composition on the surface, e.g. by distributing it over the surface ("rubbing") using a suitable instrument such as for instance a brush or in the case of surfaces to be cleaned of small objects also by stirring the object in a liquid cleaning composition. Optionally, a further step of leaving the cleaning composition to stand on the surface can follow. Finally, the cleaning composition is removed, e.g. by rinsing with water and drying the surface with compressed air. The duration of the moving cleaning step is preferably 10 to 60 seconds, particularly preferably 10 to 30 seconds. The duration of the standing step is preferably 5 to 45 seconds, particularly preferably 5 to 25 seconds.

The present invention also relates to the use of the cleaning composition according to the invention to clean a dental restoration or an implant abutment. If the overall method of restoring a tooth using a cleaning step according to the invention is considered, this preferably comprises the steps:

(a) inserting a dental restoration into a tooth cavity, onto a tooth stump or onto an implant abutment to check the accuracy of fit, (b) removing the dental restoration from the oral cavity, (c) cleaning the dental restoration and/or intraorally cleaning the implant abutment with the cleaning composition according to the invention as described above, preferably by rubbing the cleaning composition on the dental restoration or the implant abutment with a brush, leaving the cleaning composition to stand, rinsing off the cleaning composition with distilled water and drying the dental restoration or the implant abutment with compressed air, and (d) adhesively securing the dental restoration in the oral cavity in the tooth cavity, on the tooth stump or on the implant abutment.

The dental restoration is typically adhesively secured by means of customary adhesion promoters ("primers") and radically curing fixing cements and composites; however, an adhesive securing not using primers is also possible. Suitable fixing cements, composites and primers are known from the state of the art and described for example in Resin-ceramic bonding: a review of the literature: Blatz et al., "Resin-Ceramic Bonding: A Review of the Literature," *J. Prosthet. Dent.* 89:268-74 (2003); Kitayamaa et al., "Effect of Primer Treatment on Bonding of Resin Cements to Zirconia Ceramic," *Dent. Mat.* 2009, Article in Press, which are hereby incorporated by reference in their entirety

EXAMPLES

The present invention is now explained in more detail below by means of examples which are not meant to be limiting.

Example 1—Preparation of the Cleaning Compositions According to the Invention

The cleaning compositions given in Table 1 were prepared by weighing the components into a receptacle and mixing them by exposure to the action of an ultrasonic dispersion device for approximately 10 minutes (UP200S; Hielscher Ultraschalltechnik, Teltow, Germany).

TABLE 1

Cleaning compositions

| Composition | Cleaning particles (20 g) | Carrier medium (80 g) | Appearance |
|---|---|---|---|
| ERM-I | Boehmite powder[1] (25 nm) | Dist. water | slightly opaque, strongly thixotropic gel |
| ERM-II | $ZrO_2$ powder[2] (12 ± 3 nm) | 1M NaOH, pH 14 | white opaque, weakly thixotropic, sedimentation-stable dispersion |
| ERM-III | $ZrO_2$ powder[2] (12 ± 3 nm) | Boric acid-caustic soda buffer solution, pH 11 | white opaque, weakly thixotropic, sedimentation-stable dispersion |
| ERM-IV | $ZrO_2$ powder[2] (12 ± 3 nm) | Sodium tetraborate-caustic soda buffer solution, pH 10 | white opaque, weakly thixotropic, sedimentation-stable dispersion |
| ERM-V | $ZrO_2$ powder[2] (12 ± 3 nm) | Tris-acetate buffer solution, pH 8 | white opaque, weakly thixotropic, sedimentation-stable dispersion |
| ERM-VI | Rutile powder[3] (10-30 nm) | 1M NaOH, pH 14 | white opaque, weakly thixotropic, sedimentation-stable dispersion |

[1]Disperal P2W, weight-average particle size = 25 nm; SASOL, Johannesburg, South Africa
[2]ZirCOX™ 15, weight-average particle size = 12 ± 3 nm; IBU-Tec, Weimar, Germany
[3]nanoparticulate rutile, weight-average particle size = 10-30 nm, Io-Li-Tec, Denzlingen, Germany Example 2—Determination of the Cleaning Effect a) Sample Preparation Cuboidal testpieces from different materials used in dental medicine were prepared closely following the protocol described in Dtsch Zahnärztl Z 48:769-772 (1993), which is hereby incorporated by reference in its entirety. The cuboidal testpieces were surface-ground with SiC abrasive paper of grit size P120-P400-P1000 accompanied by water cooling.

The individual substrate surfaces were then conditioned as follows, according to the corresponding manufacturer's instructions, i.e. silicious surfaces were etched with hydrofluoric acid, and oxidic or metallic surfaces sandblasted with corresponding grain size and pressure.

Lithium disilicate glass ceramic (e.max CAD; Ivoclar Vivadent AG, Schaan, Liechtenstein) was brought into contact with 4.5% hydrogen fluoride etching gel for 20 seconds (Ceramic Etch, Ivoclar Vivadent AG) and then carefully rinsed with distilled water.

Zirconium dioxide ceramic (ZirCAD; Ivoclar Vivadent AG, Schaan, Liechtenstein), aluminium oxide ceramic (Al-Cube; VITA Zahnfabrik, Bad Säckingen, Germany) and pure titanium (Tritan; Dentaurum, Ispringen, Germany) were roughened with 50 μm aluminium oxide abrasive (Korox 50; BEGO, Germany) at a pressure of 2.5×105 Pa (2.5 bar) from a distance of approximately 1 to 2 cm for 15 seconds.

All samples were then cleaned for 10 min in ethanol in an ultrasonic bath. After removal from the ethanol, the samples were blown dry with compressed air and stored protected from dust until used.

b) Saliva Contamination

To simulate saliva contamination, the prepared testpieces were placed in fresh human saliva for 60 seconds, then rinsed with distilled water for 15 seconds and treated in plenty of ethanol for 60 seconds in the ultrasonic bath. The samples were dried with an air blower and further treated as described below.

c) Cleaning Method

Testpieces were cleaned with the cleaning compositions according to the invention ERM-I to ERM-VI. For comparison purposes, testpieces were used which were treated as follows:

REF: Uncontaminated reference sample
WJ: Sample after saliva contamination cleaned for 15 seconds with water jet
PAG: Sample after saliva contamination brought into contact with 37% phosphoric acid etching gel (Email Preparator, Ivoclar Vivadent AG, Liechtenstein) for 30 seconds.
PPP: Sample after saliva contamination treated with polishing paste based on pumice (Proxyt fine polishing paste; Ivoclar Vivadent AG).
NAOH Sample after saliva contamination treated with 1 M NaOH.

All cleaning compositions ERM-I to ERM-VI according to the invention and the comparison agents PPP and NAOH were moved on the testpiece with a clinically usual brush (Microbrush; USA) for 10 seconds and then left to stand for 20 seconds. In all of the cleaning methods carried out, the agents were then rinsed off with a clinically usual water jet and the testpieces were finally blown dry with oil-free compressed air from a clinically usual air blower.

d) Determination of the Bonding Values—Sample Preparation Method 1 (with Primer):

The testpieces prepared as above were given a full single coat, using the brush (Microbrush; USA), with a customary universal dental adhesion promoter (Monobond Plus adhesion promoter; Ivoclar Vivadent AG, Schaan, Liechtenstein), containing a phosphate-functionalized methacrylate, an alkoxysilane methacrylate and a disulphide methacrylate in alcoholic solution, and the liquid was allowed to act for 60 seconds. Supernatant liquid was then blown off with compressed air. As described in Kern et al., "Eine einfache Versuchsanordnung zur universellen Prüfung des Klebeverbundes im axialen Zugtest" [A Simple Method for Universal Testing of Tensile Bond Strength], Dtsch Zahnärztl Z 48:769-772 (1993), which is hereby incorporated by reference in its entirety, a plexiglas sleeve filled with light-polymerizable, dental composite material (MultiCore Flow; radically curing stump construction composite, Ivoclar Vivadent AG, Schaan, Liechtenstein) was applied to the primed surface. For this, the sleeve was covered at the end to be bonded to with a drop of radically curing fixing cement (Multilink Automix; Ivoclar Vivadent AG, Schaan, Liechtenstein) and pressed onto the testpiece by means of a press apparatus. The cement was then cured by 2×20 seconds irradiation with a polymerization lamp (Bluephase G2; Ivoclar Vivadent AG; Schaan, Liechtenstein) and the samples were stored in water for 24 hours at 37° C. The tensile adhesion was then determined as described below.

Method 2 (Without Primer):

As described in Dtsch Zahnärztl Z 48:769-772 (1993), which is hereby incorporated by reference in its entirety, a plexiglas sleeve filled with light-polymerizable, dental composite material (MultiCore Flow; radically curing stump construction composite, Ivoclar Vivadent AG, Schaan, Liechtenstein) was applied to an unprimed zirconium dioxide surface. For this, the sleeve was covered at the end to be bonded to with a drop of self-adhesive, radically curing fixing cement (SpeedCEM; Ivoclar Vivadent AG, Schaan, Liechtenstein) and pressed onto the testpiece by means of a press apparatus. The cement was then cured by 2×20 seconds irradiation with a polymerization lamp (Bluephase G2; Ivoclar Vivadent AG; Schaan, Liechtenstein) and the samples were stored in water for 24 hours at 37° C. The tensile adhesion was then determined as described below.

e) Determination of the Bonding Values—Measurement of the Adhesion

To determine the bonding values, a pull-off arrangement was used such as is described in the literature (Kern et al., "Eine einfache Versuchsanordnung zur universellen Prüfung des Klebeverbundes im axialen Zugtest" [A Simple Method for Universal Testing of Tensile Bond Strength], Dtsch Zahnärztl Z 48:769-772 (1993), which is hereby incorporated by reference in its entirety). The results listed in Table 2 were determined with a Z010 universal testing machine (Zwick-Roell, Ulm, Germany) which is structurally identical to the apparatus used by M. Kern. Seven individual samples of each group were measured and the average of the tensile adhesion calculated.

f) Results

As Table 2 shows, even after cleaning with water (group WJ), saliva contamination leads to the weakening, known in the literature, of the bond compared with uncontaminated references (group REF).

The success of a cleaning with 37% phosphoric acid gel (PAG) was substrate-dependent: while the silicate ceramic (lithium disilicate glass ceramic) from group PAG had a bonding value comparable to group REF, the bond to the zirconium dioxide ceramic achieved only half of the original value from group REF. The method is thus not suitable for all substrates, which limits the universal applicability of this method and makes it necessary for the dentist to select a cleaning method that is suitable for the respective surface.

The treatment, studied in group PPP, of the ceramic with polishing paste based on pumice was ineffective as regards the achieved bonding values. On none of the studied substrates were the bonding values significantly increased compared with the contaminated group WJ.

The treatment with ERM-I led to a significant increase in the bonding values compared with the group WJ. Scanning electron microscopy (SEM) showed that the particles have no detectable abrasion effect. The bonding values achieved in group REF were again achieved on all of the surfaces within the framework of the measuring accuracy of group ERM-I. ERM-I therefore represents an effective means, as regards bond strength, of cleaning protein-contaminated silicate and oxide ceramic as well as metal restorations in an adhesive fixing therapy.

TABLE 2

Tensile bonding values on saliva-contaminated restoration material after different cleaning processes

| Cleaning process | Substrate | Method for preparing the testpiece | Tensile adhesion [MPa] |
|---|---|---|---|
| REF*) | Zirconium dioxide | 1 | 52.1 ± 10.9 |
| | | 2 | 42 ± 19.6 |
| | Lithium disilicate glass ceramic | 1 | 55.9 ± 9.2 |
| | Pure titanium | | 31.5 ± 5.6 |
| | Aluminium oxide | | 39.4 ± 11.3 |
| WJ*) | Zirconium dioxide | 1 | 15.8 ± 16.1 |
| | | 2 | 1.4 ± 2.1 |
| | Lithium disilicate glass ceramic | 1 | 21 ± 13.6 |
| | Pure titanium | | 2.5 ± 1.9 |
| | Aluminium oxide | | 9.8 ± 2.7 |
| PAG*) | Zirconium dioxide | 1 | 26.7 ± 11.8 |
| | Lithium disilicate glass ceramic | | 40.6 ± 10.7 |
| PPP*) | Zirconium dioxide | 1 | 21.9 ± 14.2 |
| | Lithium disilicate glass ceramic | | 29.7 ± 15.2 |
| NAOH*) | Zirconium dioxide | 1 | 34.8 ± 18.4 |
| | Lithium disilicate glass ceramic | | 30.2 ± 8.4 |
| ERM-I | Zirconium dioxide | 1 | 43.9 ± 8.4 |
| | Lithium disilicate glass ceramic | | 46.0 ± 7.4 |
| | Pure titanium | | 28.2 ± 8.7 |
| | Aluminium oxide | | 50.5 ± 7.2 |
| ERM-II | Zirconium dioxide | 1 | 63.1 ± 11.6 |
| | | 2 | 42.5 ± 9.4 |
| | Lithium disilicate glass ceramic | 1 | 54.6 ± 11.9 |
| | Pure titanium | | 27.9 ± 8.6 |
| | Aluminium oxide | | 45.8 ± 10 |
| ERM-III | Zirconium dioxide | 1 | 55.4 ± 6.1 |
| | Lithium disilicate glass ceramic | | 51.2 ± 7.5 |
| ERM-IV | Zirconium dioxide | 1 | 46.7 ± 16.6 |
| | Lithium disilicate glass ceramic | | 48.7 ± 10.3 |
| ERM-V | Zirconium dioxide | 1 | 33.8 ± 9.7 |
| | Lithium disilicate glass ceramic | | 35.2 ± 9.8 |
| ERM-VI | Zirconium dioxide | 1 | 43.5 ± 9.9 |
| | Lithium disilicate glass ceramic | | 50.1 ± 6.9 |

*)Comparison examples

ERM-II was statistically significantly effective on both ceramics and produced bond strengths comparable to the initial values REF. Scanning electron microscopy (SEM) showed that the particles have no detectable abrasion effect.

Nevertheless, the bonding values after cleaning with ERM-II were surprisingly produced in full again, as Table 2 shows. ERM-II therefore represents an effective means, as regards bond strength, of cleaning protein-contaminated silicate and oxide ceramic as well as metal restorations in an adhesive fixing therapy.

The tests carried out at pH 11 in group ERM-III showed the effectiveness of ERM-III on both types of ceramic. The bonding values achieved in group ERM-III correspond to the initial values of group REF within the framework of measuring accuracy. Scanning electron microscopy (SEM) showed that the particles have no detectable abrasion effect. Nevertheless, the bonding values after cleaning with ERM-III were surprisingly produced in full again, as the table shows. The effectiveness of phosphoric acid on silicate ceramic demonstrated in group PAG was also achieved, with the result that ERM-III represents a cleaning agent that is comparable to the literature reference, but not substrate-dependent.

The tests carried out at pH 10 in group ERM-IV showed the effectiveness of ERM-IV on both types of ceramic. The bonding values achieved in group ERM-IV correspond to the initial values of group REF within the framework of measuring accuracy. Scanning electron microscopy (SEM) showed that the particles have no detectable abrasion effect. Nevertheless, the bonding values after cleaning with ERM-IV were surprisingly produced in full again, as the table shows. ERM-IV also achieved the effectiveness of phosphoric acid on silicate ceramic demonstrated in group PAG. ERM-IV therefore represents a cleaning agent that is comparable to the literature reference, but not substrate-dependent.

The tests carried out at pH 8 in group ERM-V showed the effectiveness of ERM-V on both types of ceramic. Scanning electron microscopy (SEM) showed that the particles have no detectable abrasion effect. Although, as the table shows, the cleaning with ERM-V did not produce in full the bonding values compared with group REF, the bond strength is clearly above that of the samples of group WJ cleaned only with water. ERM-V therefore represents a cleaning agent that is not substrate-dependent.

The tests of group ERM-VI showed the effectiveness, not substrate-dependent, of ERM-VI on both types of ceramic. Scanning electron microscopy (SEM) showed that the particles used here have no detectable abrasion effect. Nevertheless, the bonding values after cleaning with ERM-VI were surprisingly produced in full again, as the table shows, and correspond to the initial values of the group REF within the framework of measuring accuracy. The effectiveness of phosphoric acid on silicate ceramic demonstrated in group PAG was achieved, with the result that ERM-VI represents a cleaning agent that is comparable to the literature reference, but not substrate-dependent.

The test of group NAOH carried out with pure caustic soda, without nanoparticulate component, showed a clearly lower effectiveness on both types of ceramic. The bonding values of the group NAOH are clearly lower than the initial values of the group REF. Bearing in mind that group ERM-II had a very great cleaning effect at the same pH, this proves the surprisingly positive influence of suitable nanoparticles on the surface cleaning.

Although various embodiments have been depicted and described in detail herein, it will be apparent to those skilled in the relevant art that various modifications, additions, substitutions, and the like can be made without departing from the spirit of the disclosure and these are therefore considered to be within the scope of the subject matter as defined in the claims which follow.

What is claimed:

1. A method for cleaning dental materials contaminated with bodily fluids, comprising steps in the following order:
    inserting a dental restoration into a tooth cavity, onto a tooth stump or onto an implant abutment in an oral cavity to check accuracy of fit;
    removing the dental restoration from the oral cavity;
    applying a composition onto a metal or ceramic surface of the dental restoration, wherein the composition comprises 1 to 75 wt.-% particles with a weight-average particle diameter of 1 to 500 nm based on a metal compound which is selected from metals of the $3^{rd}$ main group, subgroup metals and lanthanoids of the Periodic Table, and 25 to 99 wt.-% water or aqueous solution with a pH in the range from at least 8 to 14, wherein the particles of the composition interact with phosphate groups of the bodily fluids;
    rinsing the surface with water to remove the composition, and
    securing the metal or ceramic surface to the tooth cavity, tooth stump, or implant abutment located in the oral cavity.

2. The method according to claim 1, wherein the surface to be cleaned is contaminated by proteins.

3. The method according to claim 2, wherein the surface to be cleaned is contaminated by saliva proteins.

4. The method according to claim 1, wherein the cleaning takes place immediately after a try-in of the dental restoration.

5. The method according to claim 1, wherein the metal of the metal compound is selected from aluminium, zirconium, titanium, scandium, yttrium, zinc, ytterbium, cerium and combinations thereof.

6. The method according to claim 5, wherein the metal compound is selected from metal chalcogenides; metal halides; metal chalcogen halides; metal pseudohalides; metal-silicon chalcogenides; metal hydroxides; metal oxyhydroxides, metal nitrates, metal oxynitrates and mixtures thereof.

7. The method according to claim 6, wherein the metal compound is selected from aluminium oxide, aluminium oxide hydroxide, zirconium dioxide, titanium dioxide and mixtures thereof.

8. The method according to claim 1, wherein the carrier medium is a liquid.

9. The method according to claim 1, wherein the particles are present in a quantity of 1 to 50 percent by weight relative to the total weight of the composition.

10. The method according to claim 1, wherein the surface to be cleaned comprises an oxide ceramic, a silicate ceramic, titanium or a titanium alloy.

11. The method according to claim 1, wherein the particles have a weight-average particle diameter of 1 to 100 nm.

12. The method according to claim 1, wherein the carrier medium is a solid.

13. The method according to claim 1, wherein the particles are present in a quantity of 5 to 35 percent by weight relative to the total weight of the composition.

14. The method according to claim 1, wherein the particles of the composition bond to proteins in the bodily fluids for removal from the surface.

15. The method according to claim 14, wherein the bond comprises adsorption, ionic bonding and/or covalent bonding.

16. A method for cleaning dental materials, comprising steps in the following order:
    inserting a dental restoration into a tooth cavity, onto a tooth stump or onto an implant abutment in an oral cavity to check accuracy of fit;
    removing the dental restoration from the oral cavity;
    applying a composition onto a metal or ceramic surface of the dental restoration, wherein the composition comprises 1 to 75 wt.-% particles with a weight-average particle diameter of 1 to 500 nm based on a metal compound which is selected from metals of the $3^{rd}$ main group, subgroup metals and lanthanoids of the Periodic Table, and 25 to 99 wt.-% water or aqueous solution with a pH in the range from at least 8 to 14, wherein applying is performed by stirring the metal or ceramic surface in the composition or contacting the metal or ceramic surface with a brush;
    rinsing the surface with water to remove the composition, and securing the metal or ceramic surface to the tooth cavity, tooth stump, or implant abutment located in the oral cavity.

17. The method according to claim 1, wherein the securing step comprises adhesion by one or more of an adhesive promoter, a cement, or a composite.

18. The method according to claim 17, wherein the adhesive promoter comprises a self-adhesive and/or a primer.

19. The method according to claim 16, wherein the securing step comprises adhesion by one or more of an adhesive promoter, a cement, or a composite.

20. The method according to claim 19, wherein the adhesive promoter comprises a self-adhesive and/or a primer.

* * * * *